United States Patent [19]

Baba et al.

[11] Patent Number: 4,931,565

[45] Date of Patent: Jun. 5, 1990

[54] PROCESS FOR PRODUCTION OF 2-PYRAZOLIN-5-ONES

[75] Inventors: Masatoshi Baba; Norio Tanaka; Hideo Suzuki, all of Funabashi, Japan

[73] Assignee: Nissan Chemical Industries, Ltd., Tokyo, Japan

[21] Appl. No.: 342,703

[22] Filed: Apr. 20, 1989

Related U.S. Application Data

[63] Continuation of Ser. No. 32,625, Apr. 1, 1987, abandoned.

[30] Foreign Application Priority Data

Apr. 2, 1986 [JP]  Japan ................................. 61-76287

[51] Int. Cl.⁵ ........................................... C07D 231/20
[52] U.S. Cl. .................................... 548/363; 546/279; 548/364; 548/367
[58] Field of Search ....................... 548/363, 367, 364; 546/279

[56] References Cited

U.S. PATENT DOCUMENTS 3,957,814  5/1976  Moller et al. ....................... 548/363

FOREIGN PATENT DOCUMENTS 268659  11/1986  Japan ................................. 548/363

Primary Examiner—Robert W. Ramsuer
Attorney, Agent, or Firm—Oliff & Berridge

[57] ABSTRACT

A process for production of 2-pyrazolin-5-ones having the formula (I):

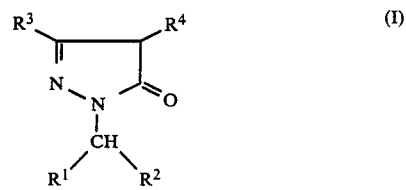

which comprises cyclizing hydrazone derivatives having the formula (II):

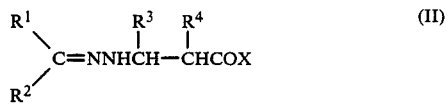

in the presence of a base;
wherein $R^1$, $R^2$, $R^3$ and $R^4$ each represents a specific group; compounds having the formula (I) as well as compounds having the formula (II) and a process for production thereof.

4 Claims, No Drawings

PROCESS FOR PRODUCTION OF 2-PYRAZOLIN-5-ONES

This is a continuation of Ser. No. 032,625, filed 4/1/87 now abandoned.

BACKGROUND OF THE INVENTION

1. Field of the Invention

The present invention relates to novel 2-pyrazolin-5-ones and a novel process for production thereof as well as novel hydrazone derivatives which are intermediates for synthesis of the aforesaid 2-pyrazolin-5-ones and a process for production thereof.

2. Brief Description of the Prior Art

2-Pyrazolin-5-ones are useful as intermediate raw materials for drugs represented by antipyrine and various investigations have been hitherto made also on a process for production thereof.

In recent years, it has become clear that 2-pyrazolin-5-ones are also useful as intermediate raw materials for herbicides (U.S. Pat. No. 4,063,925, U.S. Pat. No. 4,230,481, U.S. Pat. No. 4,406,688 and U.S. Pat. No. 4,557,753) which are a series of compounds that are expected to expand their applicable range more in the future.

As a process for production of such 2-pyrazolin-5-ones, for example, the following reaction is known:

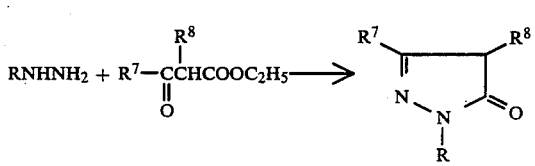

(1)

wherein $R^7$ represents, e.g., a lower alkyl group; $R^8$ represents, e.g., a hydrogen atom or a lower alkyl group; and R represents, e.g., a hydrogen atom, a methyl group or a phenyl group.

This reaction is a process for obtaining the desired 2-pyrazolin-5-ones from mono-substituted hydrazines and β-keto esters at one step, which generally gives a high yield and is an excellent process.

However, a problem of this process lies in that there is a restriction in access to the raw β-keto esters and monosubstituted hydrazines.

For example, 1-substituted-2-pyrazolin-5-ones which are most typical 2-pyrazolin-5-ones wherein $R^7$ and $R^8$ represent hydrogen atoms are not prepared by this process because formylacetic acid ester used as a raw material thereof is unstable.

In addition, mono-substituted hydrazines shown by $RNHNH_2$ are not easily accessible, except for some of hydrazines in which R is a phenyl ring, an aromatic hetero ring and a methyl group; after all, 2-pyrazolin-5-ones which can be produced at low costs are restricted also in this aspect.

A reaction shown by:

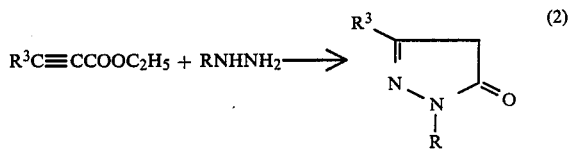

(2)

is also known.

According to this reaction, however, compounds which are easily prepared are restricted due to difficult accessibility to the mono-substituted hydrazines as in the case of (1), acetylenecarboxylic acid esters as another raw materials are not necessarily readily accessible in an inexpensive way, by-products are generally easily produced and as a result, the yield is not always high and purification is not easy. After all, it should be said that industrial practicability is poor.

For the reasons described above, notwithstanding that investigations have been made on the process for production of 2-pyrazolin-5-ones over long years and, for example, many 3-methyl-2-pyrazolin-5-ones have been synthesized, 3,4-unsubstituted 2-pyrazolin-5-ones are a series of novel compounds that have not been synthesized yet except for several compounds.

These exceptional several compounds were synthesized by the process shown below:

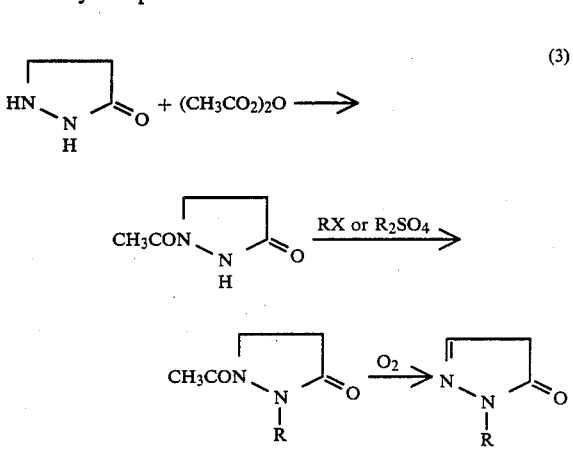

(3)

(Dorn. Hetall, J. Prakt. Chem., 115 (1971)).

According to this process, compounds wherein R is methyl and benzyl can be prepared. However, this process is not preferred because the N atom on the pyrazoline ring should be once protected by an acetyl group, alkylation also occurs on the oxygen atom and therefore the reaction becomes complicated and, removal of the by-products and acetic acid by-products is also troublesome, etc.

Further, the synthesis of 1-(p-chlorobenzyl)-2-pyrazoline is reported in U.S. Pat. No. 3,952,008. The synthesis is based on the process (2) described above and not preferred for the reasons described above.

Furthermore, the process shown in (4) has been developed in recent years.

(4)

-continued

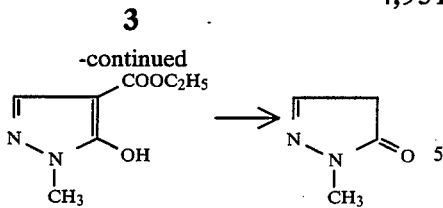

This process is superior to the process (3) but inferior to the process of the present invention in view of operations and costs because methylhydrazine is much more expensive than the unsubstituted hydrazines used in the present invention, ethoxymethylenemalonic acid diester is also expensive, an isomer:

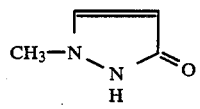

is by-produced, etc.

In addition, the scope of the substituent R capable of easily producing 2-pyrazolin-5-ones is narrow due to difficult accessibility to the mono-substituted hydrazines described in (1) so that this process is far inferior to the process of the present invention.

SUMMARY OF THE INVENTION

An object of the present invention is to provide a novel process for production of novel 2-pyrazolin-5-ones using readily accessible raw materials only.

Another object of the present invention is to provide novel 2-pyrazolin-5-ones obtained by the process described above.

A further object of the present invention is to provide novel hydrazone derivatives which are intermediates for producing the aforesaid 2-pyrazolin-5-ones.

A fourth object of the present invention is to provide a process for production of the novel hydrazone derivatives described above.

The novel 2-pyrazolin-5-ones of the present invention are useful as intermediates for drugs and agricultural chemicals, in particular, active ingredients of herbicidal compositions for use of paddy fields.

DETAILED DESCRIPTION OF THE INVENTION

The present invention relates to a process for production of the 2-pyrazolin-5-ones of the general formula (I):

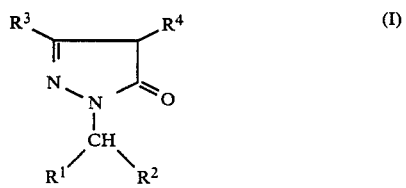

wherein $R^1$ and $R^2$ each represents a hydrogen atom, an alkyl group which may be substituted with a halogen atom or a lower alkoxy group, an alkenyl group, a lower alkoxycarbonyl group, a formyl group, a phenyl group which may be substituted, a naphthyl group which may be substituted, an aralkyl group which may be substituted or a hetetrocyclic group which may be substituted; $R^1$ and $R^2$ together with the carbon atom to which they attach may form a ring. The substituents for the phenyl group, naphthyl group, aralkyl group and heterocyclic group defined above are a halogen atom, a lower alkyl group which may be substituted with a halogen atom, a lower alkenyl group, a lower alkoxy group, a cyano group, a nitro group, a lower alkoxycarbonyl group, a carboxyl group or $-NR^5R^6$. $R^3$ represents a hydrogen atom, a lower alkyl group or a lower alkoxycarbonyl group. $R^4$ represents a hydrogen atom or a lower alkyl group. $R^5$ and $R^6$ each represents a hydrogen atom, a lower alkyl group or a lower alkenyl group and, $R^5$ and $R^6$ together with the nitrogen atom to which they attach may form a ring; which comprises cyclizing hydrazone derivatives of the general formula (II):

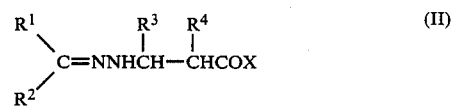

wherein $R^1$, $R^2$, $R^3$ and $R^4$ have the meanings defined above; and X represents a lower alkoxy group or $-NR^5R^6$ wherein $R^5$ and $R^6$ have the meanings defined above, in the presence of a base.

Further the present invention also relates to a process for production of the hydrazone derivatives of the general formula (II) used in the reaction described above. The process for production of the hydrazone derivatives comprises condensing hydrazine derivatives of the general formula (III):

with ketones or aldehydes of the general formula (IV):

In general formulae (III) and (IV) described above, $R^1$, $R^2$, $R^3$ and $R^4$ and X have the same meanings defined above.

The present invention can be expressed by the following reaction equation:

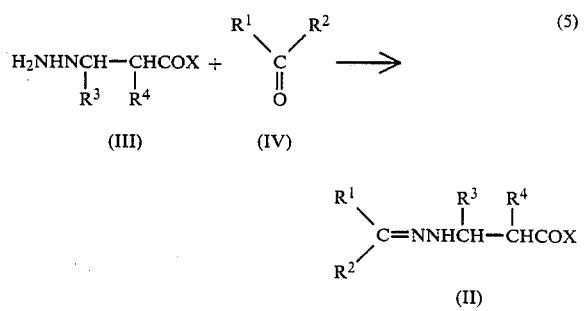

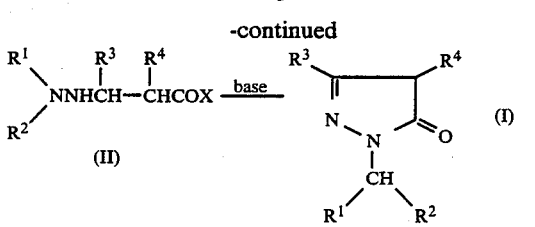

wherein $R^1$, $R^2$, $R^3$, $R^4$ and X have the same meanings defined above.

The reaction (5) shows a reaction which comprises condensing compounds (III) capable of readily producing by adding inexpensive and readily accessible unsubstituted hydrazines to acrylic acid esters or acrylamides, with ketones or aldehydes.

The reaction can be carried out in the absence of any solvent or in a solvent inert to the reaction.

In the case of using solvents, there is no particular restriction except for carbonyl compounds or acids reactive with the hydrazines but alcohols such as methanol, ethanol, isopropanol, etc.; halogenated hydrocarbons such as chloroform, methylene chloride, carbon tetrachloride, dichloroethane, trichloroethylene, etc.; aromatic hydrocarbons such as benzene, toluene, xylene, etc.; hydrocarbons such as n-hexane, cyclohexane, etc.; ethers such as tetrahydrofuran, dioxane, diethyl ether, etc. acetonitrile, N,N-dimethylformamide, dimethylsulfoxide can give good results.

There is no particular restriction to reaction temperature; the reaction temperature can be freely chosen generally from room temperature to a boiling point of a solvent.

Examples of X include methoxy group, ethoxy group, n-propoxy group, isopropoxy group, n-butoxy group, secondary-butoxy group, isobutoxy group, tertiary-butoxy group, n-amyloxy group, isoamyloxy group, tertiary-amyloxy group, n-hexyloxy group, cyclohexyloxy group, 2-ethylhexyloxy group, n-octyloxy group, isononyloxy group, n-decyloxy group, n-dodecyloxy group, n-tridecyloxy group, 2-hydroxyethyloxy group, 2-hydroxypropyloxy group, tetrahydrofurfuryloxy group, stearyloxy group, 2-methoxyethyloxy group, ethoxyethoxyethoxy group, butoxyethoxy group, methoxyethoxyethoxy group, dimethylamino group, diethylamino group, di-n-propylamino group, diisopropylamino group, di-n-butylamino group, diisobutylamino group, diallylamino group, di-secondary-butylamino group, N-ethyl-N-isopropylamino group, N-ethyl-N-methylamino group, N-ethyl-N-tertiary-butylamino group, N-methyl-N-n-butylamino group, N-ethyl-N-n-butylamino group, isobutylamino group, n-propylamino group, tertiary-butylamino group, tertiary-amylamino group, secondary-butylamino group, isopropylamino group, ethylamino group, piperidino group, pyrrolidino group, etc.

The hydrazone (II) produced by this reaction can be purified generally by means of distillation, column chromatography or recrystallization but can also be provided for the subsequent reaction as it is without purification.

Further in case that $R^1$ and $R^2$ are not the same group, the produced hydrazones (II) may be in the form of a mixture of syn-form and anti-form sometimes; also in this case, both gives the same product (I) in the subsequent reaction (6) and therefore, there is no necessity of separating them from each other.

Next, the reaction shown by (6) will be described.

In this reaction, the hydrazones (II) formed in (5) are cyclized in the presence of bases to lead to the desired 2-pyrazolin-5-ones.

In the reaction, any particular solvent is not necessarily required and the desired product can be given by adding the bases with heating but, a solvent inert to the reaction can also be employed. In some case, the yield may be increased by the use of the solvent.

Preferred examples of the solvent include alcohols such as methanol, ethanol, isopropanol, n-butanol, etc.; ethers such as tetrahydrofuran, dioxane, etc.; acetonitrile, and the like. Among them, alcohols having 1 to 6 carbon atoms and acetonitrile are particularly easy to use.

Further the substituent X in the reaction (6) has not restriction but those exemplified in (5) are usable but particularly preferred examples of X include ethoxy group, isopropoxy group, isobutoxy group, secondary-butoxy group, tertiary-butoxy group, tertiary-amyloxy group dimethylamino group, diethylamino group, tertiary-butylamino group and tertiaryamylamino group.

It is appropriate that the reaction temperature be generally at 50° to 200° C. The reaction is generally completed in 1 to 30 hours.

Examples of the bases which can be used include inorganic salts such as sodium hydroxide, potassium hydroxide, lithium hydroxide, calcium hydroxide, potassium carbonate, sodium carbonate, sodium bicarbonate, etc.; alkoxides such as sodium methoxide, sodium ethoxide, sodium butoxide, potassium butoxide, etc.; sodium hydride, sodium amide, etc. Further examples include organic amines such as triethylamine, 1,5-diazabicylo(4,3,0)-nonene (DBN), 1,8-diazabicyclo-7-undecene (DBU), 1,4-diazabicyclo(2,2,2)octane (DABCO), pyridine, etc.

Of these bases, in view of yield and costs, generally preferred are sodium hydroxide, potassium hydroxide, sodium methoxide, sodium ethoxide, sodium butoxide, etc.

The addition amount of the base is not particularly limited but approximately 1 to 3 mols of the base is preferred, more preferably 1 to 2 mols, based on 1 mol of the hydrazones (II).

After completion of the reaction, the product is obtained in the salt form as a matter of course but by neutralizing with an suitable acid (for example, hydrochloric acid), the product can also be converted into the free 2-pyrazolin-5-ones; alternatively, the product can also be taken out as the salts with the acid used for the neutralization (for example, the hydrochloride).

According to the present invention, a series of reactions of the reactions (5) and (6) including the reaction corresponding to the synthesis of the raw materials shown by:

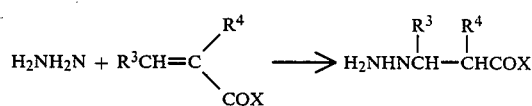

but the formed compounds may not necessarily be purified or isolated in any step; it is also possible to conduct any 2 steps or 3 steps in one pot.

The 2-pyrazolin-5-ones referred to in the present invention form tautomerism with 5-hydroxypyrazoles (V) as shown by the following equation (7):

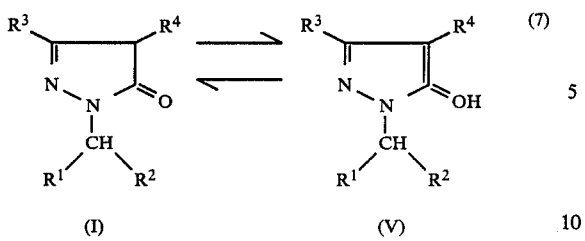

and can be expressed by any form; for purpose of simplicity, the products are expressed in the present invention as the 2-pyrazolin-5-ones which are a keto-form, throughout the specifications.

By the process described above, the various 2-pyrazolin-5ones can be synthesized by easy operations using inexpensive and readily accessible raw materials.

In particular, the 2-pyrazolin-5-ones unsubstituted at the 3-position thereof can be extremely easily synthesized according to the process of the present invention, while only several compounds could have be exceptionally synthesized heretofore due to difficulty in synthesis.

The compounds of the general formula (I), wherein both $R^3$ and $R^4$ are hydrogen atom, which can be obtained by the process described above are novel compounds except for some of them. Further the compounds of the formula (II) are novel compounds. Therefore, the present invention is also encompassed to cover and call for these novel compounds.

In general formula (I),compounds wherein $R^1$, $R^2$, $R^3$ and $R^4$ have the the same meanings defined above; with the proviso that, if $R^1$ represents a hydrogen atom, $R^2$ does not represent a hydrogen atom, a phenyl group or a p-chlorophenyl group are novel compounds.

In the compounds of the formulae (I) and (II), preferred compounds are as follows, from viewpoints of proceeding the reaction described above and giving useful compounds using the products of the present invention as raw materials:

(1) In general formulae (I) and (II), compounds wherein $R^1$ and $R^2$ each represents a hydrogen atom, an alkyl group having 1 to 4 carbon atoms which may be substituted with a lower alkoxy group; a benzyl group, a pyridyl group, a thienyl group; or a phenyl group which may be substituted with a halogen atom, a lower alkyl group, a cyano group or a di-lower alkylamino group; some of $R^1$ and $R^2$ together with the carbon atom to which they attach may form a ring.

(2) In the following formulae (I) and (II), compounds wherein $R^3$ represents a hydrogen atom.

(3) In the formulae (I) and (II), compounds wherein specifically the compounds wherein $R^1$ and $R^2$ have the same meanings defined in (1) and $R^3$ represents a hydrogen atom.

Some of the important compounds which are synthesized by the process of the present invention are shown below.

(1) 1-Ethyl-2-pyrazolin-5-one

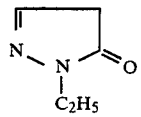

(2) 1-Isopropyl-2-pyrazolin-5-one

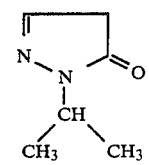

(3) 1-n-Propyl-2-pyrazolin-5-one

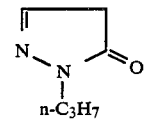

(4) 1-sec-Butyl-2-pyrazolin-5-one

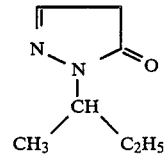

(5) 1-(1,2-Dimethylpropyl)-2-pyrazolin-5-one

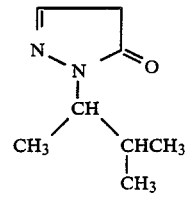

(6) 1-(Cyclopentyl)-2-pyrazolin-5-one

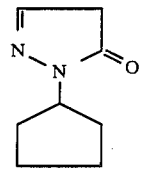

(7) 1-(Cyclohexyl)-2-pyrazolin-5-one

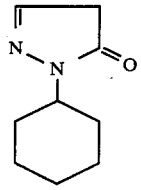

(8) 1-Benzyl-2-pyrazolin-5-one

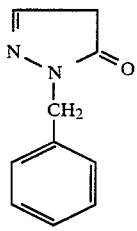

(9) 1-(2-Phenethyl)-2-pyrazolin-5-one

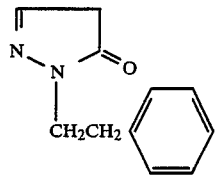

(10) 1-(2-Methoxyethyl)-2-pyrazolin-5-one

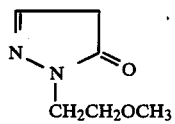

(11) 1-(2-Picolyl)-2-pyrazolin-5-one

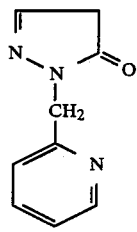

(12) 1-(2-Thenyl)-2-pyrazolin-5-one

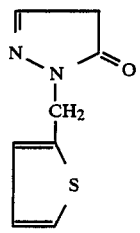

(13) 1-(2,2-Dimethylpropyl)-2-pyrazolin-5-one

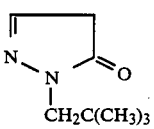

(14) 1-(p-Cyanobenzyl)-2-pyrazolin-5-one

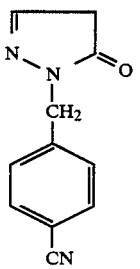

(15) 1-(2,3-Dichlorobenzyl)-2-pyrazolin-5-one

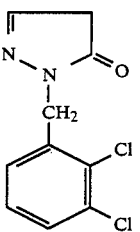

(16) 1-(m-Methoxybenzyl)-2-pyrazolin-5-one

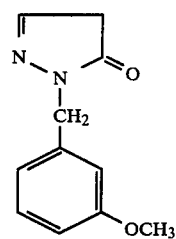

(17) 1-(p-Dimethylaminobenzyl)-2-pyrazolin-5-one

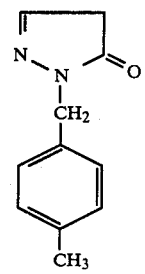

(18) 1-(p-Chlorobenzyl)-2-pyrazolin-5-one

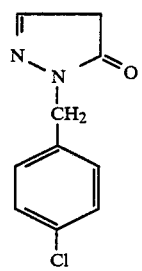

(19) 1-(p-Carboxybenzyl)-2-pyrazolin-5-one

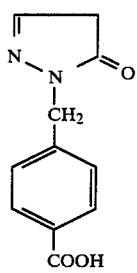

(20) 1-Ethyl-3-methyl-2-pyrazolin-5-one

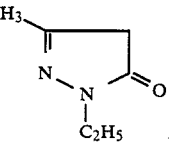

(21) 1-Ethyl-4-methyl-2-pyrazolin-5-one

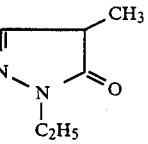

(22) 1-Methyl-2-pyrazolin-5-one

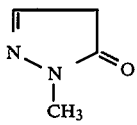

As examples of application of the compounds in accordance with the present invention as intermediates, the following reactions are shown. Compounds having herbicidal activity can be obtained by the reactions described below.

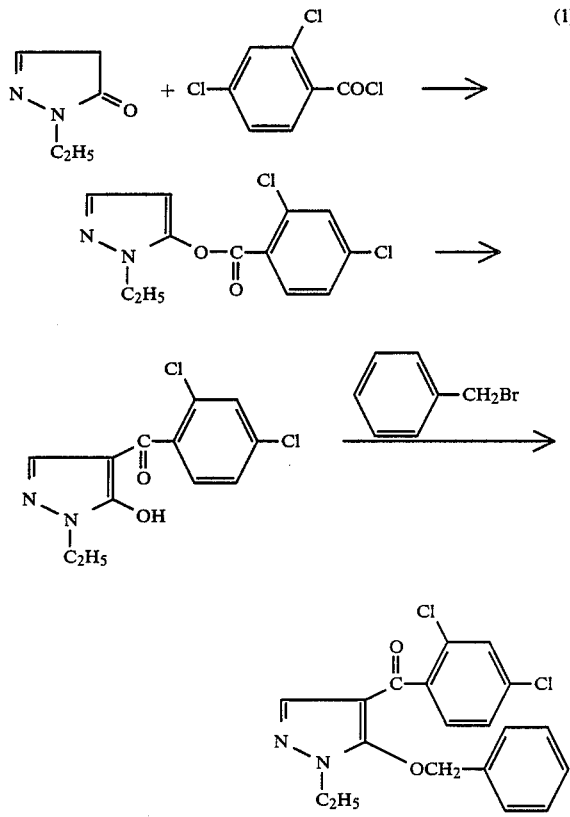

(U.S. Ser. No. 860,199 filed May 6, 1986, now U.S. Pat. No. 4,744,815)

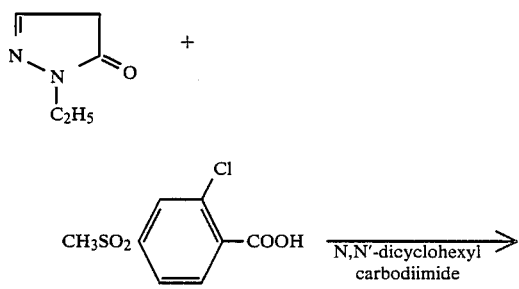

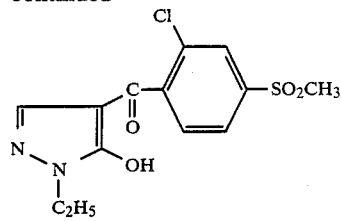

(U.S. Ser. No. 860,199 filed on May 6, 1986, now pending)

Next, the present invention will be described with reference to concrete examples below but is not deemed to be limited thereto.

REFERENCE EXAMPLE 1

Synthesis of β-hydrazinopropionic acid-tert-butyl ester

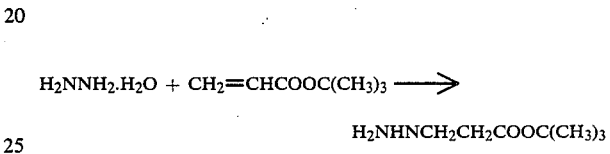

In a 4-necked reaction flask of 2 liters were charged 125 g (2 mols) of 80% hydrated hydrazine and 1 liter of ethanol. While stirring under reflux on an oil bath at 100° C., 128 g (1 mol) of tert-butyl acrylate was dropwise added to the mixture over 10 minutes. After stirring was continued for further 10 minutes, the reaction was completed. Subsequently, the solvent was removed from the reaction solution by distillation, 143 g (0.83 mols) of the fraction at a boiling point of 65° to 67° C. was obtained by distillation under reduced pressure of 0.5 mmHg.

EXAMPLE 1

Synthesis of acetaldehyde-β-tert-butoxycarbonylethyl hydrazone

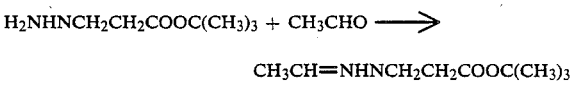

To 50 ml of methanol was added 16.0 g (0.1 mol) of tert-butyl β-hydrazinopropionate. The mixture was stirred at room temperature. Further 5.5 g (0.1 mol) of 81% acetaldehyde was dropwise added thereto over 30 minutes. During the addition, the system was exothermic and the temperature raised to approximately 50° C.

After the solvent was removed by distillation under reduced pressure, the residue was fractionated to give a fraction showing a boiling point of 70° to 77° C./0.15 mmHg. NMR analysis revealed that the product was acetaldehyde-β-tert-butoxycarbonylethyl hydrazone (syn- and anti-mixture). Yield, 91%.

$^1$H-NMR 1.43 (s), 1.66 (d), 1.81 (d), 2.27–2.67 (m), 3.07–3.56 (m), 3.9–5.0(broad), 6.55 (q), 6.98 (q), [solvent, CDCl$_3$].

EXAMPLE 2

Synthesis of acetaldehyde-β-tert-butoxycarbonylethyl hydrazone

Using 100 ml of chloroform instead of 150 ml of methanol in Example 1, the system was treated in a similar manner. After completion of the reaction, the chloroform solution was washed 3 times with water and then dried over anhydrous sodium sulfate. Thereafter, chloroform was removed by distillation under reduced pressure to give 17.3 g of the title compound (syn- and anti-mixture

EXAMPLE 3

Synthesis of 1-ethyl-2-pyrazolin-5-one

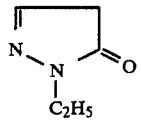

To 50 ml of ethanol was added 2.4 g of metallic sodium to convert into sodium ethoxide completely. Then, 14.9 g of acetaldehyde-$\beta$-tert-butoxycarbonylethyl hydrazone was added thereto. The mixture was heated and continued to reflux for 6 hours.

After completion of the reaction, ethanol was removed by distillation under reduced pressure and then the residue was dissolved in water. Further an excess of hydrochloric acid was added to the solution. After water was again removed by distillation under reduced pressure, ethanol was added to remove it by distillation. This operation was repeated 3 times.

Finally ethanol was added and insoluble matters were filtered off. Removal of ethanol by distillation gave 10.5 g of the hydrochloride of the title compound. Yield, 88%.

$^1$H-NMR ($\delta$, ppm, CDCl$_3$-DMSO- d$_6$); 1.46 (3H, t, J=7.2 Hz), 4.26 (2H, q, J=7.2 Hz), 5.99 (1H, d, J=3 Hz), 7.94 (1H, d, J=3 Hz).

Thereafter the hydrochloride described above was neutralized with potassium hydrogencarbonate to make the title compound free. Melting point: 212°-217° C.

EXAMPLE 4

Synthesis of acetaldehyde-N,N-dimethylcarbamoylethyl hydrazone

H$_2$NHNCH$_2$CH$_2$CON(CH$_3$)$_2$ + CH$_3$CHO $\longrightarrow$

CH$_3$CH=NHNCH$_2$CH$_2$CON(CH$_3$)$_2$

Using 13.1 g of $\beta$-hydrazino-N,N-dimethylpropionamide instead of 16.0 g of tert-butyl $\beta$-hydrazinopropionate, the system was treated in quite the same manner in example 1.

Boiling point: 104°-106° C./0.07 mmHg; Yield, 87%.

$^1$H-NMR revealed that the product was a syn- and anti-mixture of the title compound.

EXAMPLE 5

Synthesis of acetaldehyde-N,N-dimethylcarbamoylethyl hydrazone

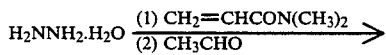

-continued

To 100 ml of methanol was added 10.0 g (0.2 mols) of 100% hydrated hydrazine. The mixture was stirred and 19.8 g (0.2 mols) of N,N-dimethylacrylamide was dropwise added thereto at room temperature over an hour. After completion of the dropwise addition, stirring was continued for further 30 minutes. Thereafter 14.1 g of 81% acetaldehyde was dropwise added thereto over 30 minutes.

After completion of the dropwise addition, stirring was continued for further an hour followed by treatment similar to Example 1. Thus 21.7 g of the title compound was obtained. Yield, 69%.

EXAMPLE 6

Synthesis of 1-ethyl-2-pyrazolin-5-one

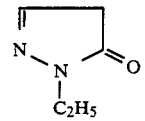

Using 12.6 g of acetaldehyde-N,N-dimethylcarbamoylethyl hydrazone instead of 14.9 g of acetaldehyde-$\beta$-tert-butoxycarbonylethyl hydrazone in Example 3, quite the same treatment was performed to give 11.3 g of the hydrochloride of the title compound. Yield, 95%.

EXAMPLE 7

Synthesis of 1-ethyl-2-pyrazolin-5-one

The system was treated in a manner similar to Example 6 except that the solvent was changed from methanol to isopropanol and the base was changed from sodium ethoxide to 6.9 g of potassium hydroxide (85%). Thus 11.4 g of the hydrochloride of the title compound. Yield, 96%.

EXAMPLE 8

Synthesis of 1-ethyl-2-pyrazolin-5-one

To 12.6 g of acetaldehyde-N,N-dimethylcarbamoylethyl hydrazone was added 3.5 g (93%) of sodium hydroxide. The mixture was heated at approximately 120° C. for 8 hours with stirring. Then, the system was treated in a manner similar to Example 3 to give 9.9 g of the hydrochloride of the title compound. Yield, 83%.

EXAMPLES 9 to 69

Synthesis of:

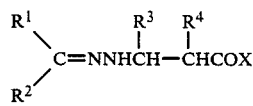

Examples 9 to 69 are shown in the following Tables 1 and 2.

In Table 1, raw materials used and kind of the products (hydrazones) as well as the mode of reaction used are shown.

In Table 2, kind of solvent, method for purification and physical properties and yield of the products are shown.

Reaction mode A)

The reaction was carried out in quite the same manner as in Example 1 except that the solvent, the hydrazine derivative and carbonyl compound reacted were changed. Then, the product was purified in a suitable manner to give the hydrazone derivative, respectively.

Reaction mode (B)

The reaction was carried out in a manner similar to Example 5 except that the solvent, the acryl acid derivative and carbonyl compound reacted were changed and the reaction temperature and reaction time with the hydrazine were chosen, respectively. Then, the product was purified in a suitable manner to give the hydrazone derivative.

Reaction mode (C)

In a 4-necked reaction flask of 300 ml were charged 12.5 g (0.2 mols) of 80% hydrated hydrazine and 100 g of ethanol. While stirring under reflux on an oil bath at 100° C., 0.1 mol of various esters of acrylic acid was dropwise added to the mixture over approximately 3 minutes. After stirring was continued for further 10 minutes, the reaction was completed. Subsequently, 40 g of ethanol, 0.8 g of sodium bicarbonate, 3 g (0.1 mol) of paraformaldehyde were added followed by stirring at 50° C. for 15 minutes. After completion of the reaction, the system was concentrated and then distilled thereby to give the hydrazone derivative.

TABLE 1

Synthesis of Hydrazones $$\begin{matrix} R^1 \\ R^2 \end{matrix} C=O + H_2NHNCH(R^3)-CHCOX(R^4) \longrightarrow \begin{matrix} R^1 \\ R^2 \end{matrix} C=NNHCH(R^3)-CHCOX(R^4)$$

| Example No. | $R^1$ | $R^2$ | $R^3$ | $R^4$ | X | Reaction Mode |
|---|---|---|---|---|---|---|
| 9 | $C_2H_5$ | H | H | H | TBO | A |
| 10 | $CH_3$ | $CH_3$ | H | H | DMA | B |
| 11 | $C_2H_5$ | $CH_3$ | H | H | TBO | A |
| 12 | $(CH_3)_2CH$ | $CH_3$ | H | H | DMA | B |
| 13 | $(CH_3)_3C$ | $CH_3$ | H | H | DMA | B |
| 14 | $-(CH_2)_4-$ | | H | H | TBO | A |
| 15 | $-(CH_2)_5-$ | | H | H | DMA | B |
| 16 | $COOC_2H_5$ | $CH_3$ | H | H | TBO | A |
| 17 | Phenyl | H | H | H | DMA | B |
| 18 | Benzyl | H | H | H | DMA | B |
| 19 | p-Nitrophenyl | H | H | H | DMA | B |
| 20 | Phenyl | $CH_3$ | H | H | DMA | B |
| 21 | Cyclohexyl | H | H | H | DMA | B |
| 22 | Formyl | $CH_3$ | H | H | DMA | B |
| 23 | $CH_3$ | H | H | $CH_3$ | TBO | B |
| 24 | $CH_3$ | H | $CH_3$ | H | TBO | B |
| 25 | H | H | $COOC_2H_5$ | H | $COOC_2H_5$ | A |
| 26 | $CH_3$ | H | $COOCH(CH_3)_2$ | H | $COOCH(CH_3)_2$ | B |
| 27 | $CH_3$ | H | $CH_2COO(CH_2)_3CH_3$ | H | $COO(CH_2)_3CH_3$ | A |
| 28 | $CH_3OCH_2$ | H | H | H | DMA | B |
| 29 | $CH_3$ | H | $C_2H_5$ | H | TBO | A |
| 30 | p-Methylphenyl | H | H | H | TBO | A |
| 31 | 2-Furyl | H | H | H | DMA | B |
| 32 | $(CH_3)_3C$ | H | H | H | DMA | B |
| 33 | 2-Thienyl | H | H | H | DMA | B |
| 34 | p-Methoxy-carbonyl phenyl | H | H | H | DMA | B |
| 35 | 2-Pyridyl | H | H | H | DMA | B |
| 36 | p-Cyanophenyl | H | H | H | DMA | B |
| 37 | $CH_2=CHCH_2CH_2$ | $CH_3$ | H | H | DMA | B |
| 38 | $CH_3$ | H | H | H | $N[CH(CH_3)_2]_2$ | B |
| 39 | $CH_3$ | H | H | H | $NHC(CH_3)_3$ | B |
| 40 | $CH_3$ | H | H | H | $NHC(CH_3)_2C_2H_5$ | B |
| 41 | $CH_3$ | $CH_3$ | H | H | $NHC(CH_3)_3$ | B |
| 42 | H | H | $CH_3$ | H | $NHC(CH_3)_3$ | B |
| 43 | p-Nitrophenyl | $CH_3$ | H | H | DMA | B |
| 44 | p-Dimethyl-aminophenyl | H | H | H | DMA | B |
| 45 | m-Methoxy-phenyl | H | H | H | DMA | B |
| 46 | H | H | H | $CH_3$ | TBO | B |
| 47 | 2,3-Dichloro-phenyl | H | H | H | DMA | B |
| 48 | α-Naphthyl | H | H | H | DMA | B |
| 49 | p-Methyl-phenyl | H | H | H | DMA | B |
| 50 | p-Chloro-phenyl | H | H | H | DMA | B |
| 51 | o-Trifluoro-methylphenyl | H | H | H | DMA | B |
| 52 | Styryl | H | H | H | DMA | B |

TABLE 1-continued

Synthesis of Hydrazones $$\begin{array}{c} R^1 \\ \diagdown \\ R^2 \end{array} C=O + H_2NHNCH-CHCOX \xrightarrow{R^3\ R^4} \begin{array}{c} R^1 \\ \diagdown \\ R^2 \end{array} C=NNHCH-CHCOX$$

| Example No. | R¹ | R² | R³ | R⁴ | X | Reaction Mode |
|---|---|---|---|---|---|---|
| 53 | p-Carboxyphenyl | H | H | H | DMA | B |
| 54 | H | H | H | H | TBO | A |
| 55 | H | H | H | H | OC₂H₅ | C |
| 56 | H | H | H | H | OCH(CH₃)₂ | C |
| 57 | H | H | H | H | OCH₂CH(CH₃)₂ | C |
| 58 | H | H | H | H | OCH(CH₃)C₂H₅ | C |
| 59 | H | H | H | H | OC(CH₃)₂C₂H₅ | C |
| 60 | H | H | H | H | DMA | A |
| 61 | H | H | H | H | NHC(CH₃)₃ | A |
| 62 | H | H | H | H | N(C₂H₅)₂ | A |
| 63 | H | H | H | H | N[CH(CH₃)₂]₂ | A |
| 64 | H | H | H | H | NHC(CH₃)₃ | B |
| 65 | H | H | H | H | DMA | B |
| 66 | H | H | H | H | N(C₂H₅)₂ | B |
| 67 | H | H | H | H | N(C₃H₇)₂ | B |
| 68 | H | H | H | H | NHC(CH₃)₂C₂H₅ | B |
| 69 | H | H | H | H | N(CH₂CH=CH₂)₂ | B |

TABLE 2

Yield and Physical Properties of Hydrazones

| Example No. | Solvent | Purification | Property | Yield (%) |
|---|---|---|---|---|
| 9 | Methanol | D | b.p. 144–147° C./20 mmHg | 83 |
| 10 | Methanol | D | b.p. 126° C./0.26 mmHg | 51 |
| 11 | Methanol | D | b.p. 82–87° C./0.2 mmHg | 93 |
| 12 | Methanol | D | b.p. 123° C./0.1 mmHg | 54 |
| 13 | Methanol | D | b.p. 138–140° C./1.5 mmHg | 40 |
| 14 | Methanol | D | b.p. 105–111° C./0.2 mmHg | 84 |
| 15 | Methanol | D | b.p. 164–166° C./0.6 mmHg | 56 |
| 16 | Methanol | D | b.p. 115–123° C./0.15 mmHg | 84 |
| 17 | Methanol | R | m.p. 119–121° C. | 51 |
| 18 | Methanol | C | oily substance | 90 |
| 19 | Methanol | R | m.p. 175–178° C. | 61 |
| 20 | Methanol | — | oily substance | 75 |
| 21 | Methanol | D | b.p. 160–162° C./0.25 mmHg | 60 |
| 22 | Methanol | C | oily substance | 41 |
| 23 | Methanol | D | b.p. 82–87° C./0.2 mmHg | 19 |
| 24 | Methanol | D | b.p. 69–78° C./0.2 mmHg | 77 |
| 25 | Methanol | D | | 11 |
| 26 | Methanol | D | b.p. 103–113° C./0.2 mmHg | 70 |
| 27 | Methanol | D | b.p. 160–164° C./0.2 mmHg | 27 |
| 28 | Methanol | D | b.p. 139–141° C./0.2 mmHg | 54 |
| 29 | Methanol | D | b.p. 74–76° C./0.25 mmHg | 79 |
| 30 | Methanol | — | — | 93 |
| 31 | Methanol | C | oily substance | 25 |
| 32 | Methanol | D | b.p. 118–120° C./0.12 mmHg m.p. 52° C. | 51 |
| 33 | Methanol | R | m.p. 130–131° C. | 63 |
| 34 | Methanol | R | m.p. 151–154° C. | 53 |
| 35 | Methanol | R | m.p. 90–92° C. | 42 |
| 36 | Methanol | C | m.p. 125–126° C. | 37 |
| 37 | Methanol | D | b.p. 131–134° C./1.2 mmHg | 62 |
| 38 | Methanol | D | b.p. 95–96° C./0.1 mmHg | 59 |
| 39 | Methanol | D | b.p. 103° C./0.1 mmHg | 67 |
| 40 | Methanol | D | b.p. 117–119° C./0.09 mmHg | 63 |
| 41 | Methanol | D | b.p. 111–113° C./0.2 mmHg m.p. 68–71° C. | 84 |
| 42 | Methanol | D | b.p. 104–106° C./0.15 mmHg | 58 |
| 43 | Methanol | R | m.p. 121–123° C. | 57 |
| 44 | Methanol | R | m.p. 109–113° C. (dec.) | 67 |
| 45 | Methanol | C | m.p. 77–80° C. | 32 |
| 46 | Methanol | D | b.p. 78–81° C./2 mmHg | 44 |
| 47 | Methanol | C | oily substance | 54 |
| 48 | Methanol | C | oily substance | 38 |
| 49 | Methanol | R | m.p. 113–115° C. | 71 |
| 50 | Methanol | R | m.p. 100–101° C. | 49 |
| 51 | Methanol | R | m.p. 66–68° C. | 38 |
| 52 | Methanol | R | m.p. 106–109° C. | 51 |
| 53 | Methanol | R | m.p. 192–194° C. | 41 |
| 54 | Methanol | D | b.p. 65–67° C./0.8 mmHg | 85 |
| 55 | Ethanol | D | b.p. 65–70° C./0.35 mmHg | 49 |
| 56 | Ethanol | D | b.p. 52–68° C./0.3 mmHg | 52 |
| 57 | Ethanol | D | b.p. 75–78° C./0.3 mmHg | 57 |
| 58 | Ethanol | D | b.p. 74–76° C./0.3 mmHg | 76 |
| 59 | Ethanol | D | b.p. 79–81° C./0.3 mmHg | 68 |
| 60 | Methanol | D | b.p. 126–127° C./0.2 mmHg | 71 |
| 61 | Methanol | D | b.p. 113° C./0.25 mmHg | 95 |
| 62 | Methanol | D | b.p. 101–102° C./0.16 mmHg | 85 |
| 63 | Methanol | D | b.p. 106–108° C./0.11 mmHg | 91 |
| 64 | Methanol | D | — | 66 |
| 65 | Methanol | D | — | 54 |
| 66 | Methanol | D | — | 76 |
| 67 | Methanol | D | b.p. 116–117° C./0.1 mmHg | 51 |
| 68 | Methanol | D | b.p. 112–116° C./0.06 mmHg | 65 |
| 69 | Methanol | D | b.p. 121–123° C./0.3 mmHg | 68 |

In Tables 1 and 2 at a column entitled "X", TBO and DMA represent tert-butoxy group and dimethylamino group, respectively.

Further at a column entitled "Purification", D, R and C represent purification by distillation, recrystallization and silica gel chromatography, respectively.

EXAMPLES 70 TO 125

Synthesis of:

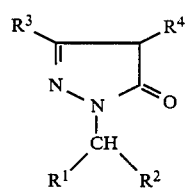

using 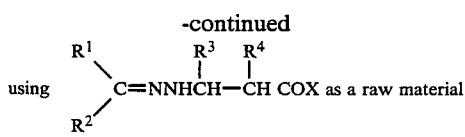 C=NNHCH—CH COX as a raw material

-continued

The hydrazone as a raw material, solvent and base were treated in a manner similar to Example 3 to give the desired 2-pyrazolin-5-one.

The results are shown in Tables 3 and 4.

In Table 3, the raw materials used, kind of the products (2-pyrazolin-5-ones), kind of solvent and base, method for determination of yield and the yield are shown.

TABLE 3

| Example No. | $R^1$ | $R^2$ | $R^3$ | $R^4$ | X | Solvent | Base | Determination of Yield | Yield (%) |
|---|---|---|---|---|---|---|---|---|---|
| 70 | H | H | H | H | TBO | i-Propanol | KOH | A | 92 |
| 71 | H | H | H | H | TBO | i-Propanol | NaOH | B | 88 |
| 72 | H | H | H | H | TBO | i-Propanol | i-PrONa | A | 100 |
| 73 | H | H | H | H | TBO | n-Propanol | n-PrONa | A | 98 |
| 74 | H | H | H | H | TBO | i-Propanol | i-PrOLi | A | 100 |
| 75 | H | H | H | H | TBO | i-Propanol | t-BuOK | A | 100 |
| 76 | H | H | H | H | TBO | Methanol | $CH_3ONa$ | A | 87 |
| 77 | H | H | H | H | TBO | Methanol | NaOH | A | 85 |
| 78 | H | H | H | H | TBO | Methanol | DBU | A | 56 |
| 79 | H | H | H | H | TBO | t-Butanol | NaOH | A | 54 |
| 80 | H | H | H | H | TBO | i-Amyl alcohol | NaOH | A | 74 |
| 81 | H | H | H | H | TBO | Acetonitrile | NaH | A | 71 |
| 82 | H | H | H | H | TBO | Ethanol | Triethylamine | A | 71 |
| 83 | H | H | H | H | TBO | Ethanol | EtONa | A | 100 |
| 84 | H | H | H | H | $OCH(CH_3)_2$ | i-Propanol | NaOH | C | 41 |
| 85 | H | H | H | H | $OCH_2CH(CH_3)_2$ | i-Propanol | NaOH | C | 76 |
| 86 | H | H | H | H | $OCH(CH_3)C_2H_5$ | i-Propanol | NaOH | C | 81 |
| 87 | H | H | H | H | $OC(CH_3)_2C_2H_5$ | i-Propanol | NaOH | C | 89 |
| 88 | H | H | H | H | DMA | Methanol | NaOH | A | 53 |
| 89 | H | H | H | H | DMA | Ethanol | NaOH | A | 68 |
| 90 | H | H | H | H | DMA | i-Propanol | NaOH | A | 60 |
| 91 | H | H | H | H | DMA | i-Propanol | KOH | A | 77 |
| 92 | H | H | H | H | DMA | Ethanol | KOH | A | 64 |
| 93 | H | H | H | H | DMA | Ethanol | NaOEt | A | 72 |
| 94 | H | H | H | H | DMA | Acetonitrile | NaH | A | 65 |
| 95 | H | H | H | H | $NHC(CH_3)_2C_2H_5$ | i-Propanol | KOH | A | 60 |
| 96 | H | H | H | H | $NHC(CH_3)_3$ | Ethanol | KOH | A | 65 |
| 97 | H | H | H | H | $N(C_2H_5)_2$ | Ethanol | EtONa | A | 61 |
| 98 | H | H | H | H | $N(C_2H_5)_2$ | i-Propanol | KOH | A | 64 |
| 99 | H | $C_2H_5$ | H | H | TBO | Ethanol | EtONa | A | 87 |
| 100 | $CH_3$ | $CH_3$ | H | H | DMA | Ethanol | EtONa | A | 74 |
| 101 | $CH_3$ | $CH_3$ | H | H | DMA | i-Propanol | KOH | A | 48 |
| 102 | $CH_3$ | $C_2H_5$ | H | H | TBO | n-Butanol | EtONa | A | 40 |
| 103 | $CH_3$ | $CH(CH_3)_2$ | H | H | DMA | n-Butanol | EtONa | A | 66 |
| 104 | $CH_3$ | $C(CH_3)_3$ | H | H | DMA | n-Butanol | NaOH | A | 8 |
| 105 | | $—(CH_2)_4—$ | H | H | TBO | n-Butanol | EtONa | A | 8 |
| 106 | | $—(CH_2)_5—$ | H | H | DMA | n-Butanol | KOH | A | 54 |
| 107 | H | Phenyl | H | H | DMA | n-Butanol | EtONa | A | 87 |
| 108 | H | Benzyl | H | H | DMA | n-Butanol | KOH | A | 45 |
| 109 | $CH_3$ | Phenyl | H | H | DMA | n-Butanol | KOH | A | 5 |
| 110 | H | Cyclohexyl | H | H | DMA | n-Butanol | KOH | A | 8 |
| 111 | H | $CH_3$ | H | $CH_3$ | TBO | Ethanol | EtONa | A | 84 |
| 112 | H | $CH_3$ | $CH_3$ | H | TBO | Ethanol | EtONa | A | 78 |
| 113 | H | $CH_3$ | $COOCH(CH_3)_2$ | H | TBO | i-Propanol | iPrONa | A | 11 |
| 114 | H | Methoxymethyl | H | H | DMA | n-Butanol | NaOH | A | 80 |
| 115 | H | 2-Pyridyl | H | H | DMA | i-Propanol | KOH | A | 75 |
| 116 | H | 2-Thienyl | H | H | DMA | i-Propanol | KOH | A | 39 |
| 117 | H | $C(CH_3)_3$ | H | H | DMA | i-Propanol | KOH | A | 98 |
| 118 | H | $C(CH_3)_3$ | H | H | DMA | Ethanol | EtONa | A | 95 |
| 119 | H | p-Cyanophenyl | H | H | DMA | n-Butanol | n-BuONa | A | 30 |
| 120 | H | 2,3-Dichlorophenyl | H | H | DMA | n-Butanol | KOH | A | 22 |
| 121 | H | m-Methoxyphenyl | H | H | DMA | n-Butanol | KOH | A | 42 |
| 122 | H | p-Dimethylaminophenyl | H | H | DMA | i-Propanol | KOH | A | 88 |
| 123 | H | p-Methylphenyl | H | H | DMA | i-Propanol | KOH | A | 78 |
| 124 | H | p-Chlorophenyl | H | H | DMA | i-Propanol | KOH | A | 66 |
| 125 | H | p-Carboxy- | H | H | DMA | n-Butanol | NaOH | A | 45 |

TABLE 3-continued

| Example No. | R[1] | R[2] | R[3] | R[4] | X | Solvent | Base | Determination of Yield | Yield (%) |
|---|---|---|---|---|---|---|---|---|---|
| | | phenyl | | | | | | | |

In Table 3, TBO and DMA at a column entitled "X" indicate tert-butoxy group and dimethylamino group, respectively.

At a column entitled "Determination of Yield", A indicates the yield obtained by converting the product into the hydrochloride and then determining the yield from its weight. Further B indicates the yield obtained by neutralizing to convert into a free state and then determining from its weight in the free state. C indicates the yield obtained by quantitative determination in the sodium salt state by liquid chromatography (internal standard; biphenyl).

The mol number of the base based on 1 mol of the hydrazone in Table 3 is 2.0 mols in the case of Examples 91 and 95, 1.5 mols in the case of Example 98 and 1.3 mols in all the other remaining examples.

Physical properties (melting points) and $^1$H-NMR values of the 2-pyrazolin-5-ones obtained in various examples shown in Table 3 are summarized in Table 4.

TABLE 4

| $R_1$ | $R_2$ | $R_3$ | $R_4$ | Isolated State | Melting Point (°C.) | $^1$H-NMR (δ, ppm), [Solvent Measured] |
|---|---|---|---|---|---|---|
| H | H | H | H | Free | 112–114 | 3.55 (3H, s), 5.27 (1H, d, J=2.5Hz), 7.07 (1H, d, J=2.5Hz), 9.08 (1H, s) [CDCl$_3$-DMSO-d$_6$] |
| H | C$_2$H$_5$ | H | H | Hydrochloride | — | 0.91 (3H, t, J=7Hz), 1.89 (2H, hexalet. J=7Hz) 4.13 (2H, t, J=7Hz), 5.92 (1H, d, J=3Hz), 7.61–7.85 (1H) [CDCl$_3$-DMSO-d$_6$] |
| CH$_3$ | CH$_3$ | H | H | Hydrochloride | — | 1.57 (6H, d, J=7Hz), 4.83 (1H, qq), 5.98 (1H, d, J=3Hz), 7.91 (1H, d, J=3Hz), [CDCl$_3$-DMSO-d$_6$] |
| CH$_3$ | C$_2$H$_5$ | H | H | Hydrochloride | 80–85 | 0.79 (3H, t, J=7Hz), 1.54 (3H, d, J=7Hz), 2.00 (2H, pentalet, J=7Hz), 4.55 (1H, hexalet, J=7Hz), 5.92 (1H, d, J=3Hz), 7.87 (1H, d, J=7Hz) [CDCl$_3$-DMSO-d$_6$] |
| CH$_3$ | CH(CH$_3$)$_2$ | H | H | Hydrochloride | — | 0.71 (3H, d, J=6Hz), 1.02 (3H, d, J=6Hz), 1.56 (3H, d, J=7Hz), 5.94 (1H, d, J=3Hz), 7.96 (1H, d, J=3Hz), [CDCl$_3$-DMSO-d$_6$] |
| | —(CH$_2$)$_4$— | H | H | Hydrochloride | — | 1.42–2.42 (8H, m), 4.34–5.12 (1H, m), 5.65 (1H, d, J=3Hz), 7.45 (1H, d, J=3Hz), [CDCl$_3$-DMSO-d$_6$] |
| | —(CH$_2$)$_5$— | H | H | Hydrochloride | — | 1.05–2.05 (10H, m), 4.40 (1H, m), 5.92 (1H, d, J=3Hz), 7.72 (1H, d, J=7Hz), [CDCl$_3$-DMSO-d$_6$] |
| H | Phenyl | H | H | Hydrochloride | — | 5.26 (2H, s), 5.78 (1H, d, J=3Hz), 7.26 (5H, m), 7.62 (1H, d, J=3Hz) [CDCl$_3$-DMSO-d$_6$] |
| H | Benzyl | H | H | Hydrochloride | — | 3.12 (2H, t, J=7Hz), 4.29 (2H, t, J=7Hz), 5.56 (1H, d, J=3Hz), 6.95–7.25 (5H, m), 7.33 (1H, d, J=3Hz) [CDCl$_3$] |
| CH$_3$ | Phenyl | H | H | Hydrochloride | — | 1.96 (3H, d, J=7Hz), 5.82 (1H, q, J=7Hz), 5.95 (1H, d, J=3Hz), 7.18–7.48 (5H, m), 7.78 (1H, d, J=3Hz) [CDCl$_3$-DMSO-d$_6$] |
| H | Cyclohexyl | H | H | Hydrochloride | — | 0.98–2.40 (10H, m), 4.35 (1H, m), 5.99 (1H, d, J=3Hz), 7.82 (1H, d, J=3Hz), [CDCl$_3$-DMSO-d$_6$] |
| H | CH$_3$ | H | CH$_3$ | Hydrochloride | — | 1.44 (3H, t, J=7Hz), 2.13 (3H, s), 4.19 (2H, q, J=7Hz), 7.74 (1H, s) [D$_2$O] |
| H | CH$_3$ | CH$_3$ | H | Hydrochloride | — | 1.37 (3H, t, J=7Hz), 2.32 (3H, s), 4.10 (2H, q, J=7Hz), 5.83 (1H, s) [DMSO-d$_6$] |

TABLE 4-continued

| R₁ | R₂ | R₃ | R₄ | Isolated State | Melting Point (°C.) | ¹H-NMR (δ, ppm), [Solvent Measured] |
|---|---|---|---|---|---|---|
| H | CH₃ | COOCH(CH₃)₂ | H | Free | 131–134 | 1.26 (6H, d, J=7Hz), 1.37 (3H, t, J=7Hz), 4.10 (2H, q, J=7Hz), 5.17 (1H, m), 5.94 (1H, s) [CDCl₃] |
| H | CH₂OCH₃ | H | H | Hydrochloride | — | 3.30 (3H, s), 3.75 (2H, t, J=6Hz), 4.27 (2H, t, J=6Hz), 5.95 (1H, d, J=3Hz), 7.91 (1H, d, J=3Hz) [CDCl₃-DMSO-d₆] |
| H | 2-Pyridyl | H | H | Hydrochloride | 190 (decompsd.) | 5.72 (2H, s), 5.85 (1H, d, J=3Hz), 7.85 (1H, d, J=3Hz), 7.43–8.86 (4H, m) [CDCl₃-DMSO-d₆] |
| H | 2-Thienyl | H | H | Hydrochloride | Glassy | 5.46 (2H, s), 5.78 (1H, d, J=2.5Hz), 6.81–7.39 (3H, m), 7.75 (1H, d, J=2.5Hz) [CDCl₃-DMSO-d₆] |
| H | C(CH₃)₃ | H | H | Hydrochloride | — | 0.99 (9H, s), 3.98 (2H, s), 6.02 (1H, d, J=3Hz), 7.96 (1H, d, J=3Hz) [CDCl₃-DMSO-d₆] |
| H | p-Cyano-phenyl- | H | H | Hydrochloride | — | 5.46 (2H, s), 5.92 (1H, d, J=3Hz), 7.46–7.65 (4H, m), 7.76 (1H, d, J=3Hz) [CDCl₃-DMSO-d₆] |
| H | 2,3-Di-chloro-phenyl | H | H | Hydrochloride | — | 5.41 (2H, s), 5.89 (1H, d, J=3Hz), 7.12–7.61 (3H, m), 7.88 (1H, d, J=3Hz) [CDCl₃-DMSO-d₆] |
| H | m-Methoxy-phenyl | H | H | Hydrochloride | — | 3.74 (3H, s), 5.29 (2H, s), 6.91 (1H, d, J=3Hz), 6.69–7.43 (4H, m), 7.82 (1H, d, J=3Hz) [CDCl₃-DMSO-d₆] |
| H | p-Di-methyl-amino-phenyl | H | H | Hydrochloride | 113–117 | 3.16 (6H, s), 5.39 (2H, s), 5.89 (1H, d, J=3Hz), 7.75 (1H, d, J=3Hz), 7.41–7.80 (4H) [CDCl₃-DMSO-d₆] |
| H | p-Methyl-phenyl | H | H | Hydrochloride | 111–114 | 2.28 (3H, s), 5.29 (2H, s), 5.88 (1H, d, J=3Hz), 7.07 (2H, ABq), 7.31 (2H, ABq), 7.58 (1H, d, J=3Hz) [CDCl₃-DMSO-d₆] |
| H | p-Chloro-phenyl | H | H | Hydrochloride | 70–73 | 5.37 (2H, s), 5.94 (1H, d, J=3Hz), 7.29 (2H, ABq), 7.46 (2H, ABq), 7.77 (1H, d, J=3Hz) [CDCl₃-DMSO-d₆] |
| H | p-Carb-oxy-phenyl | H | H | Hydrochloride | — | 5.39 (2H, s), 5.88 (1H, d, J=3Hz), 7.25–7.93 (4H), 7.81 (1H, d, J=3Hz) [CDCl₃-DMSO-d₆] |

While the invention has been described in detail and with reference to specific embodiments thereof, it will be apparent to one skilled in the art that various changes and modifications can be made therein without departing from the spirit and scope thereof.

What is claimed is:

1. A process for production of a 2-pyrazolin-5-one having the formula (I):

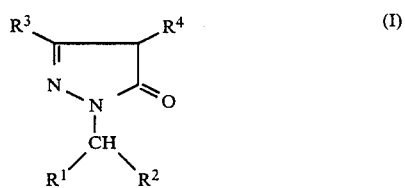

(I)

which comprises cyclizing a hydrazone derivative having the formula (II):

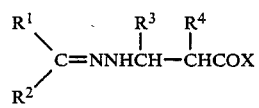

(II)

in the presence of a base;

wherein R¹ and R² each represents a hydrogen atom, an alkyl group which may be substituted with a halogen atom or a lower alkoxy group, an alkenyl group, a phenyl group which may be substituted, a naphthyl group which may be substituted, an aralkyl group which may be substituted or a hetetrocyclic group which may be substituted; R¹ and R² together with the carbon atom to which they attach may form a ring; provided that said substituents for the phenyl group, naphthyl group, aralkyl group and heterocyclic group described above include a halogen atom, a lower alkyl group which may be substituted with a halogen atom, a lower alkenyl group, a lower alkoxy group, a cyano group, a nitro group, a lower alkoxycarbonyl group, a carboxyl group or $-NR^5R^6$; $R^3$ represents a hydrogen atom, a lower alkyl group or a lower alkoxycarbonyl group; $R^4$ represents a hydrogen atom or a lower alkyl group; X represents a lower alkoxy group or $-NR^5R^6$; $R^5$ and $R^6$ described above each represents a hydrogen atom, a lower alkyl group or a lower alkenyl group and, $R^5$ and $R^6$ together with the nitrogen to which they attach may form a ring.

2. A process of claim 1 wherein $R^1$ and $R^2$ represents a hydrogen atom, an alkyl group having 1 to 4 carbon atoms which may be substituted with a lower alkyl group, a benzyl group, a pyridyl group, a thienyl group, or a phenyl group which may be substituted with a halogen atom, a lower alkyl group, a cyano group or a di-lower alkylamino group and, $R^1$ and $R^2$ together with the carbon atom to which they attach may form a ring.

3. A process of claim 1 wherein $R^3$ represents a hydrogen atom.

4. A process of claim 2 wherein $R^3$ represents a hydrogen atom.

* * * * *